United States Patent
Fout et al.

(10) Patent No.: US 8,251,936 B2
(45) Date of Patent: Aug. 28, 2012

(54) ORTHOPEDIC WALKER BOOT HAVING A REMOVABLE HEEL PLATE

(75) Inventors: James M. Fout, Oceanside, CA (US); Jeffrey R. Regan, Carlsbad, CA (US); Tiffany A. Bell, San Diego, CA (US); Paul H. Nelson, Encinitas, CA (US)

(73) Assignee: Breg, Inc., Carlsbad, CA (US)

( * ) Notice: Subject to any disclaimer, the term of this patent is extended or adjusted under 35 U.S.C. 154(b) by 537 days.

(21) Appl. No.: 12/506,260

(22) Filed: Jul. 21, 2009

(65) Prior Publication Data

US 2010/0100020 A1 Apr. 22, 2010

Related U.S. Application Data

(60) Provisional application No. 61/196,879, filed on Oct. 20, 2008.

(51) Int. Cl.
*A61F 5/00* (2006.01)
*A43B 5/00* (2006.01)

(52) U.S. Cl. .................................. 602/23; 36/25 R (58) Field of Classification Search .............. 36/92, 105, 36/83, 88, 7.1 R, 7.1 A, 24.5, 34 R, 58.5, 36/58.6, 80, 82, 72 R, 72 B, 140, 145, 166, 36/173, 25 R, 103, 104, 117.3, 113, 114, 36/115, 116, 117.1, 117.4, 117.5, 3 B, 13, 36/15, 22 R, 73; 602/13.5, 1, 23, 24, 25, 602/27, 28, 29, 32

See application file for complete search history.

(56) References Cited

U.S. PATENT DOCUMENTS

| | | |
|---|---|---|
| 3,745,998 A | 7/1973 | Rose |
| 3,955,565 A | 5/1976 | Johnson, Jr. |
| 4,057,056 A | 11/1977 | Payton |
| 4,572,169 A | 2/1986 | Mauldin et al. |
| 4,590,932 A | 5/1986 | Wilkerson |
| 4,771,768 A | 9/1988 | Crispin |
| 5,050,620 A | 9/1991 | Cooper |
| 5,078,128 A | 1/1992 | Grim et al. |
| 5,088,479 A | 2/1992 | Detoro |
| 5,329,705 A | 7/1994 | Grim et al. |
| 5,378,223 A | 1/1995 | Grim et al. |
| 5,577,998 A | 11/1996 | Johnson, Jr. et al. |
| 5,713,143 A | 2/1998 | Kendall |
| 5,762,622 A | 6/1998 | Lamont |
| 5,891,073 A | 4/1999 | Deirmendjian et al. |
| 5,957,872 A | 9/1999 | Flick |

(Continued)

OTHER PUBLICATIONS

Sroufe Healthcare Products Inc., "Pneu Gel Chevron Walking Boot", at least as early as May 2003.

(Continued)

*Primary Examiner* — Patricia Bianco
*Assistant Examiner* — Tarla Patel
(74) *Attorney, Agent, or Firm* — Rodney F. Brown (57) ABSTRACT

An orthopedic walker boot for wearing on a lower limb of a wearer has a rigid external shell, a pliant internal boot positioned in the external shell, and a heel plate selectively detachable or attachable to the external shell. Selective transition of the heel plate between the detached condition and attached condition selectively provides the orthopedic walker boot with an open-heel configuration or a closed-heel configuration. The external shell includes an outer sole having a walking surface which is configured with two curved axes to facilitate walking while wearing the orthopedic walker boot.

11 Claims, 11 Drawing Sheets

U.S. PATENT DOCUMENTS

| | | | |
|---|---|---|---|
| 6,056,712 A | 5/2000 | Grim | |
| 6,228,044 B1 * | 5/2001 | Jensen et al. | 602/27 |
| 6,251,065 B1 | 6/2001 | Kochamba et al. | |
| 6,277,087 B1 | 8/2001 | Hess et al. | |
| 6,514,222 B2 | 2/2003 | Cook | |
| 6,554,785 B1 | 4/2003 | Sroufe et al. | |
| 6,558,339 B1 | 5/2003 | Graham | |
| 6,755,798 B2 | 6/2004 | McCarthy et al. | |
| 6,866,043 B1 | 3/2005 | Davis | |
| 6,926,687 B2 | 8/2005 | Shields | |
| 8,012,112 B2 * | 9/2011 | Barberio | 602/14 |
| 2002/0083618 A1 | 7/2002 | Erickson et al. | |
| 2002/0138026 A1 | 9/2002 | Cook | |
| 2005/0070833 A1 | 3/2005 | Shields | |
| 2005/0228332 A1 | 10/2005 | Bushby | |
| 2005/0240139 A1 | 10/2005 | Bushby | |
| 2008/0269656 A1 * | 10/2008 | Arnold et al. | 602/28 |
| 2009/0247923 A1 * | 10/2009 | Lundberg | 602/27 |

OTHER PUBLICATIONS

Aircast Incorporated. "Pneumatic Walker Diabetic System". Oct. 10, 2000.

Donjoy. "MaxTrac Air Walker", at least as early as Jul. 30, 2009.

* cited by examiner

ORTHOPEDIC WALKER BOOT HAVING A REMOVABLE HEEL PLATE

This application claims the benefit of U.S. Provisional Application No. 61/196,879 filed on Oct. 20, 2008 entitled "Orthopedic Walker Having Removable Heel Plate", which is incorporated herein by reference.

BACKGROUND OF THE INVENTION

The present invention relates generally to orthopedic devices, and more particularly to orthopedic walker boots for supporting and/or immobilizing the lower limb of a wearer during activity.

Orthopedic walker boots are designed to be worn on the lower limb of a person afflicted with a lower leg, ankle, or foot injury, such as a fracture, soft tissue injury, or the like. The walker boot immobilizes and supports the injured lower limb during low-impact, weight-bearing activities such as walking and standing. The walker boot is often an effective substitute for a conventional plaster or fiberglass cast with numerous advantages. Among its advantages, walker boots are prefabricated yet are adaptable to different sized individual wearers or to variations in size of the same lower limb of a wearer over time as the lower limb is rehabilitated. In addition walker boots are more wear resistant, more comfortable to wear, and more easily cleaned than conventional casts and can be temporarily removed by the wearer for bathing, sleeping, range of motion exercise, or other non-weight-bearing activities.

Many orthopedic walker boots are known in the prior art as evidenced by the following representative U.S. Pat. No. 5,078,128 to Grim et al., U.S. Pat. No. 4,771,768 to Crispin, U.S. Pat. No. 4,572,169 to Mauldin et al., U.S. Pat. No. 4,057,056 to Payton, and U.S. Pat. No. 3,955,565 to Johnson, Jr. All of these prior art orthopedic walker boots are commonly characterized as having a rigid external shell which is the primary structural support for the lower leg, ankle, and foot of the wearer. The external shell is characterized as having either an open-heel or a closed-heel configuration. Mauldin et al. is an example of an open-heel configuration while Grim et al. is an example of a closed-heel configuration.

The open-heel configuration of the external shell exemplified by Mauldin et al. maintains the posterior face of the heel open and exposed to its external surroundings, thereby avoiding contact between the external shell of the orthopedic brace and the posterior face of the heel. This configuration is particularly advantageous in cases where there is a wound on the posterior face of the heel, such as when the wearer has undergone Achilles tendon surgery. Contact between the wound and the rigid surfaces of the external shell could irritate the wound, causing discomfort to the wearer and also prolonging the wound healing process.

The closed-heel configuration of the external shell exemplified by Grim et al. covers the posterior face of the heel. This configuration is particularly advantageous in cases where the wearer maintains an active regimen of everyday activities. The rigid surface of the external shell protects the heel in the same manner as conventional footwear to prevent potentially painful impacts against the heel by objects in the external surroundings during normal activity.

The present invention recognizes a need for an orthopedic walker boot having an external shell which can be transitioned from the closed-heel configuration to the open-heel configuration or vice versa at any time in accordance with the needs of the wearer. Accordingly, it is an object of the present invention to provide an improved orthopedic walker boot having an external shell which is readily adaptable to alternate configurations in accordance with the varying needs of the wearer. In particular, it is an object of the present invention to provide an orthopedic walker boot having an external shell which is readily adaptable to the closed-heel configuration or the open-heel configurations as desired. More particularly, it is an object of the present invention to provide an orthopedic walker boot having an external shell including a heel plate which is selectively removable by the practitioner so that the external shell adopts an open-heel configuration or which is selectively insertable by the practitioner so that the external shell adopts a closed-heel configuration.

Another common feature of the above-recited prior art orthopedic walker boots is that the external shell has an outer sole on the bottom thereof which functions as a walking platform for the foot of the wearer against the ground during normal activity. The outer sole of some of these prior art orthopedic walker boots is characterized as having an arcuate configuration. In particular, the outer sole is bowed upward along its longitudinal axis from the approximate midpoint of the external shell toward the heel and toe of the external shell. See, for example, Grim et al. and Payton.

The arcuate configuration of the outer sole is intended to enhance the ability of the wearer to walk with a more normal gait while wearing the orthopedic walker boot. In a typical normal walking gait, the heel strikes the ground first when the wearer takes a step. The foot of the wearer then flexes, the foot rolling forward along the ground with the heel disengaging the ground and the ball of the foot and toes engaging the ground. Thereafter, the entire foot disengages the ground to complete the step while the next step is simultaneously being initiated by a heel strike of the opposite foot. The outer sole on conventional footwear is generally sufficiently flexible to enable a person to roll the foot in the normal walking gait without requiring any curvature of the outer sole. However, the outer sole of prior art orthopedic walker boots are substantially bulkier and more rigid than the outer soles of conventional footwear. Therefore, the outer sole on the external shell of many prior art orthopedic walker boots is arced to facilitate the longitudinal rolling of the foot in the normal walking gait.

Although rolling of the foot along its longitudinal axis from heel to toe is an accurate characterization of the normal walking gait, the foot also rolls along its latitudinal axis, which is perpendicular to the longitudinal axis, from the medial to the lateral side of the foot or vice versa during a normal walking gait. The present invention further recognizes a need for an orthopedic walker boot having an external shell with an outer sole which is not only curved along its longitudinal axis, but is also curved along its latitudinal axis in a manner which facilitates both the longitudinal and latitudinal rolling of the foot in the normal walking gait.

Accordingly, in addition to the above-recited objects, it is an object of the present invention to provide an improved orthopedic walker boot having an external shell with an outer sole which is configured to facilitate the rolling of the foot in the normal walking gait. In particular, it is an object of the present invention to provide an improved orthopedic walker boot having an external shell with an outer sole which is curved along two different axes of its walking surface. More particularly, it is an object of the present invention to provide an orthopedic walker boot having an external shell with an outer sole which is curved along the longitudinal and latitudinal axes of its walking surface. These objects and others are accomplished in accordance with the invention described hereafter.

SUMMARY OF THE INVENTION

One characterization of the present invention is an orthopedic walker boot including an external shell and a heel plate.

The external shell is configured to receive a lower limb of a wearer. The heel plate is selectively transitionable between a detached condition and an attached condition with respect to the external shell. The external shell has an open-heel configuration when the heel plate is in the detached condition and a closed-heel configuration when the heel plate is in the attached condition. In accordance with a specific embodiment, the external shell is substantially rigid.

In accordance with a specific embodiment of the invention, the external shell has a heel plate retention segment including a retention slot and the heel plate has a guide runner. The retention slot is configured to slidably receive the guide runner therein when the heel plate is in the attached condition and to slidably discharge the guide runner when the heel plate is in the detached condition.

In accordance with another specific embodiment of the invention, the heel plate has an outside face with a protruding upper portion and a recessed lower portion. The protruding upper portion has a bottom edge and an outside surface while the recessed lower portion has an outside surface. The heel plate retention segment has an inside face, an outside face, and a top edge. The outside surface of the lower portion slidably engages the inside face of the heel plate retention segment and the bottom edge of the upper portion engages the top edge of the heel plate retention segment when the heel plate is in the attached condition.

In accordance with yet another specific embodiment of the present invention, the bottom edge of the upper portion continuously engages the top edge of the heel plate retention segment when the heel plate is in the attached condition. As such, the outside surface of the upper portion in combination with the outside face of the heel plate retention segment forms an essentially smooth continuous posterior surface of the orthopedic walker boot.

Another characterization of the present invention is an orthopedic walker boot including a rigid external shell, a selectively removable heel plate, and a pliant internal boot. The heel plate has a detached condition and an attached condition to provide the external shell with an open-heel configuration or a closed-heel configuration, respectively. The pliant internal boot is positioned in the external shell and has a foot portion, a leg portion and a heel portion. As such, the internal boot is sized to enclose an ankle, a foot, and a heel of a lower limb of a wearer. When the heel plate is in the attached condition, it is positioned adjacent to and covers the heel portion of the internal boot, thereby shielding the heel of the lower limb. When the heel plate is in the detached condition, the heel portion of the internal is uncovered by the heel plate.

Yet another characterization of the present invention is an orthopedic walker boot including an external shell configured to receive a lower limb of a wearer. The external shell includes an outer sole having a walking surface, which has two curved axes. In accordance with a specific embodiment of the invention, a first axis of the two curved axes is longitudinal and a second axis of the two curved axes is latitudinal.

Still another characterization of the present invention is an orthopedic walker boot having a rigid external shell which includes an outer sole having a walking surface. The walking surface of the external shell has a curved latitudinal axis.

The present invention will be further understood from the drawings and the following detailed description.

BRIEF DESCRIPTION OF THE DRAWINGS

The accompanying drawings illustrate certain aspects of the present invention, but should not be viewed as by themselves limiting or defining the invention.

DESCRIPTION OF PREFERRED EMBODIMENTS

Figure 1:
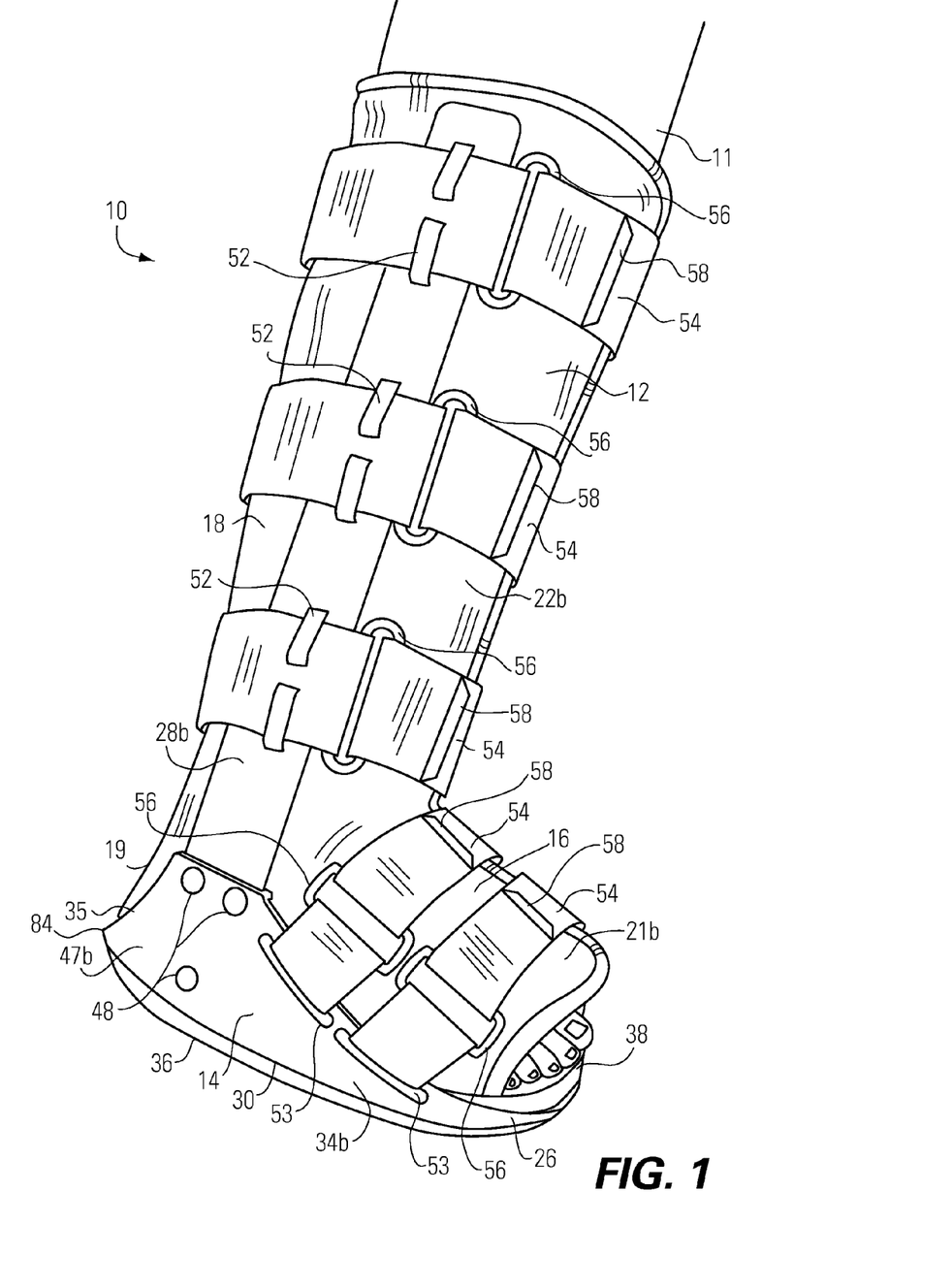
FIG. 1 is a side perspective view of an orthopedic walker boot of the present invention worn on a lower limb, wherein the orthopedic walker boot has an open-heel configuration.
Figure 2:
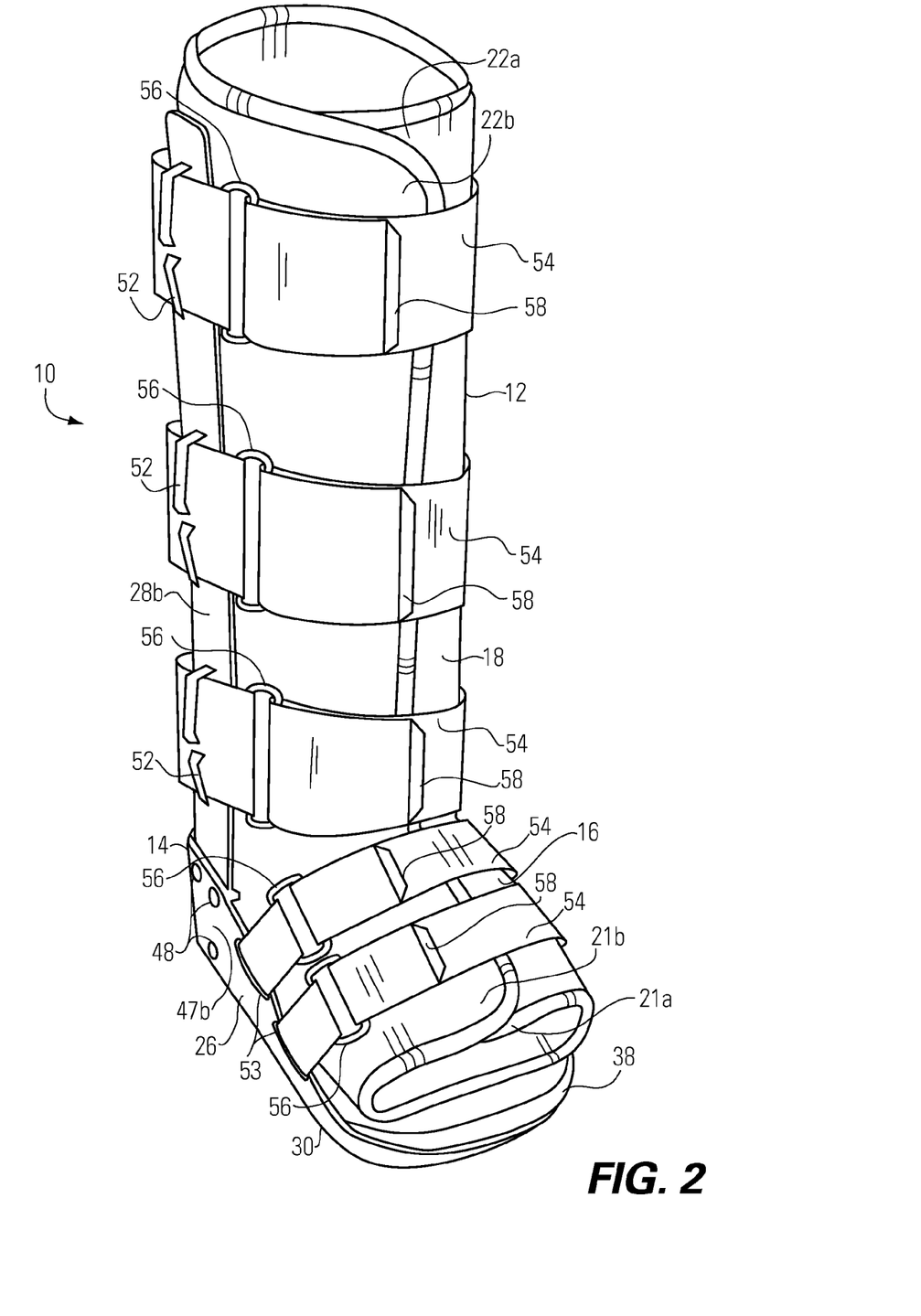
FIG. 2 is a front perspective view of the orthopedic walker boot of FIG. 1, wherein the lower limb of the wearer has been omitted for clarity.

Referring initially to FIGS. 1 and 2, an embodiment of the orthopedic walker boot of the present invention is shown and generally designated 10. The orthopedic walker boot 10 is generally sized and configured to be worn on a lower limb 11 of a person in the manner of conventional ankle-high or knee-high footwear as shown in FIG. 1. The lower limb 11 has been omitted from FIG. 2 for purposes of illustration, but it is understood that the same relationship shown in FIG. 1 between the orthopedic walker boot 10 and the lower limb 11 carries over to FIG. 2.

The orthopedic walker boot 10 comprises an internal boot 12 and an external shell 14. The internal boot 12 has a foot portion 16 which is configured to enclose the foot of the lower limb 11. As such, the foot portion 16 extends forward from the heel to the toes of the wearer's foot when the orthopedic walker boot 10 is worn on the lower limb 11. The internal boot 12 also has a lower leg portion 18 which is configured to enclose the lower leg, including the ankle, of the lower limb 11. As such, the lower leg portion 18 extends upward from the heel to a point proximal to, but below, the wearer's knee when the orthopedic walker boot 10 is worn on the lower limb 11. The internal boot 12 still further has a heel portion 19 at the intersection of the foot portion 16 and lower leg portion 18 which is configured to enclose the heel of the lower limb 11. As such, the heel portion 19 is positioned at the wearer's heel when the orthopedic walker boot 10 is worn on the lower limb 11.

FIGS. 1 and 2 show the internal boot 12 in a closed on-the-leg configuration. In accordance with the closed on-the-leg configuration, the internal boot 12 is open at its lower end to expose the toes on the foot of the lower limb 11 and at is upper end to expose the lower leg of the lower limb 11 proximal to, but below, the knee. However, the remainder of the internal boot 12, i.e., the foot, lower leg and heel portions 16, 18, and 19, which extend between the open ends of the internal boot 12, is essentially fully closed. As such, the internal boot 12 forms an essentially continuous enclosure for the lower limb 11 of the wearer when the internal boot 12 is in the closed on-the-leg configuration.

Figure 3:
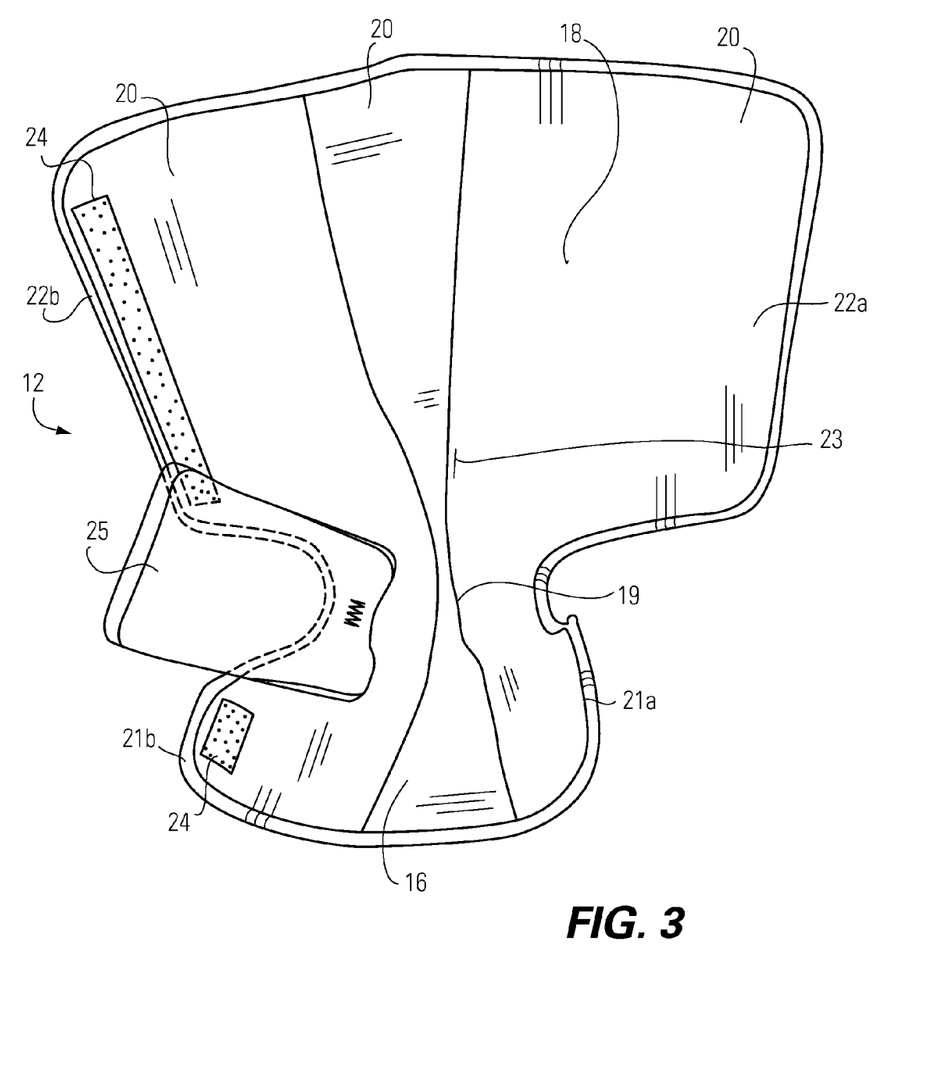
FIG. 3 is a front perspective view of an internal boot included in the orthopedic walker boot of FIG. 1, but with the internal boot having an off-the-leg configuration.

Details of the internal boot 12 are described below with reference to FIG. 3. It is noted that FIG. 3 shows the internal boot in an open off-the-leg configuration. The internal boot 12 is transitionable between the open off-the-leg configuration shown in FIG. 3 and the closed on-the-leg configuration shown in FIGS. 1 and 2 in a manner described hereafter.

The internal boot 12 is fabricated from one or more soft pliant materials, which insulate the enclosed lower limb 11 from direct contact with rigid objects external to the internal boot 12, thereby both cushioning and protecting the lower limb 11. A preferred soft pliant material for the internal boot 12 is a laminate. A laminate is defined herein as a unitary sheet formed from a plurality of planar layers of material overlaying and continuously and permanently bonded to one another across substantially their entire adjoining surfaces by means of an adhesive or the like. A preferred laminate is a cloth-foam-cloth laminate with the cloth forming the exposed faces of the laminate.

The internal boot 12 is constructed by cutting a sheet of the soft pliant material into a plurality panels 20 which are configured to conform to the dimensions of the lower limb 11 of the wearer when the panels are assembled together. Assembly of the panels 20 is effected by sewing the panels 20 together along their adjacent edges. The resulting internal boot 12 is preferably free of any supplemental support structures, such as stays, stiffeners, splints, fluid-filled bladders, or the like, which are integral with or mounted to the internal boot 12. Thus, the internal boot 12 preferably lacks any retention structures, such as stitching, pockets, straps, fasteners, or the like, which are adapted to retain any supplemental support structures.

The anterior of the internal boot 12 is provided with first and second lower flaps 21a, 21b, which are integrally configured with the foot portion 16 of the internal boot 12, and first and second upper flaps 22a, 22b, which are integrally configured with the lower leg portion 18 of the internal boot 12. The first and second lower flaps 21a, 21b and the first and second upper flaps 22a, 22b are selectively engagable with one another and disengagable from one another in a manner described hereafter. Selective engagement and disengagement of the first and second lower flaps 21a, 21b and the first and second upper flaps 22a, 22b enables the practitioner to transition the internal boot 12 between the closed on-the-leg configuration shown in FIGS. 1 and 2 and the open off-the-leg configuration shown in FIG. 3.

The internal boot 12 is preferably transitioned from the open off-the-leg configuration to the closed on-the-leg configuration after the lower limb 11 has been disposed in the interior 23 of the internal boot 12 while in the open off-the-leg configuration. The closed on-the-leg configuration is effected by overlapping the first lower flap 21a with the second lower flap 21b and correspondingly overlapping the first upper flap 22a with the second upper flap 22b. The first and second lower flaps 21a, 21b and likewise the first and second upper flaps 22a, 22b are retained in releasable overlapping engagement with one another by means of releasable fasteners, which in the present embodiment are conventional releasable hook and loop fasteners commercially available under the trade name VELCRO. The cloth forming the exterior of the internal boot 12 constitutes the loop material of the VELCRO fasteners and patches 24 affixed to the second lower and upper flaps 21b, 22b at appropriate locations thereon constitute the hook material of the VELCRO fasteners.

The anterior of the internal boot 12 is further provided with an additional flap, i.e., an enclosure flap 25, which is attached to an anterior side of the heel portion 19 of the internal boot 12. The enclosure flap 25 tucks under the opposite anterior side of the heel portion 19 when the lower flaps 21a, 21b and the upper flaps 22a, 22b are placed in overlapping engagement with one another. The enclosure flap 25 covers any gaps which may occur in the continuity of the enclosure formed by closing the lower flaps 21a, 21b and the upper flaps 22a, 22b over one another in the above-described manner. The enclosure flap 25 also supplements the cushioning provided by the lower flaps 21a, 21b and the upper flaps 22a, 22b.

The internal boot 12 is transitioned from the closed on-the-leg configuration back to the open off-the-leg configuration by selectively disengaging the lower flaps 21a, 21b and the upper flaps 22a, 22b from releasable overlapping engagement with one another. In particular, the releasable VELCRO fasteners are uncoupled, the first lower flap 21a is pulled apart from the second lower flap 21b and the first upper flap 22a is pulled apart from the second upper flap 22b. The enclosure flap 25 is also untucked from under the opposite anterior side of the heel portion 19 and pulled away therefrom. Pulling apart the flaps 21a, 21b, 22a, 22b, 25 opens up the anterior of the internal boot 12, thereby exposing the interior 23 of the internal boot 12 so that the lower limb 11 can be withdrawn therefrom.

Figures 4, 9:
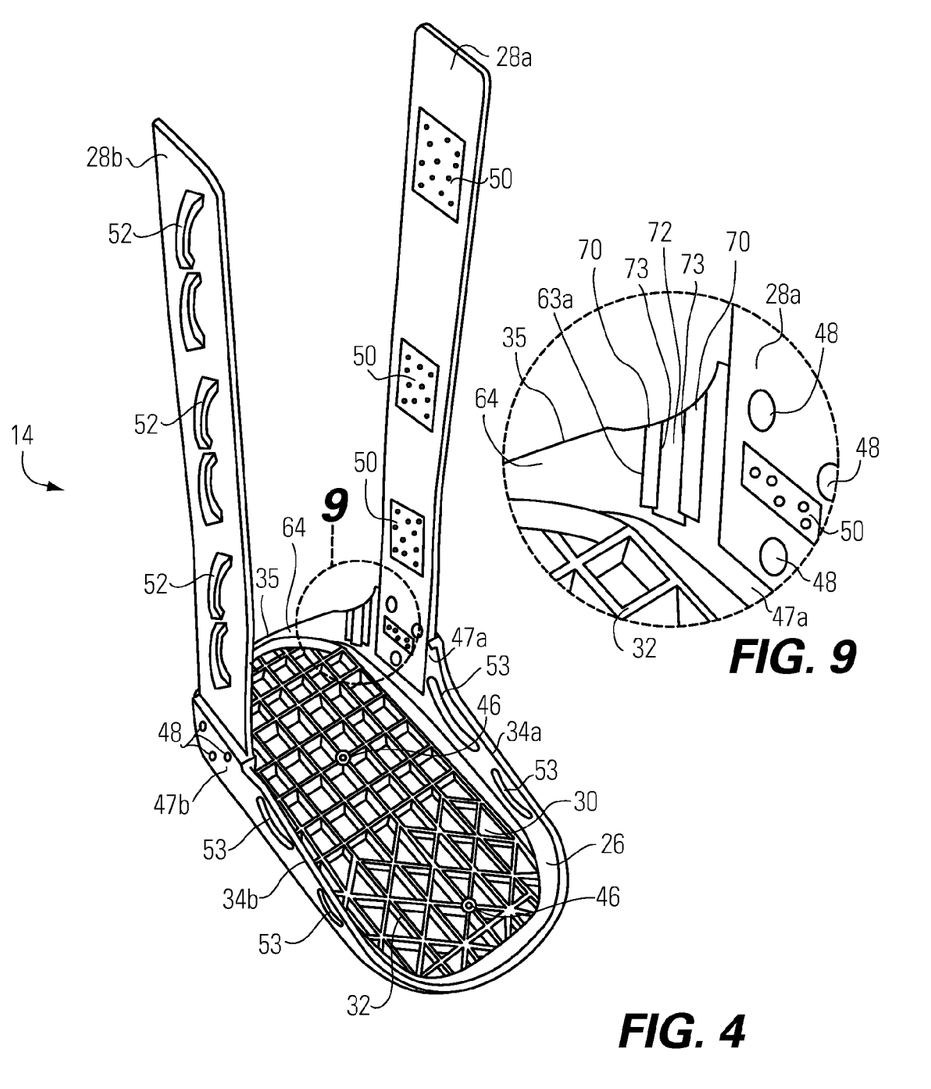
FIG. 4 is a front perspective view of an external shell included in the orthopedic walker boot of FIG. 1.
FIG. 9 is an enlarged partial view of the heel plate retention segment of the external shell of FIG. 4.

With continuing reference to FIGS. 1 and 2 and additional reference to FIG. 4, the external shell 14 of the orthopedic walker boot 10 is sized and configured in correspondence with the internal boot 12. In particular, the external shell 14 is sized and configured to receive the internal boot 12 in close fitting relationship into the external shell 14 when the internal boot 12 is in the closed on-the-leg configuration with the lower limb 11 disposed therein.

The external shell 14 comprises a base assembly 26 and first and second uprights 28a, 28b. The elements 26, 28a, 28b of the external shell 14 are formed from a hard rigid material, such as metal, molded plastic, or fiberglass, which is preferably further characterized as being high-strength and light-weight. The terms "pliant" and "rigid" as used herein are relative terms. A rigid material, such as the material of the external shell 14, has sufficient stiffness to substantially support and/or immobilize the lower limb 11 so that a wearer having the affected lower limb 11 can engage in low-impact activities such as walking or standing without substantially stressing or otherwise further negatively affecting the lower limb 11. Conversely, a pliant material, such as the material of the internal boot 12, by itself does not sufficiently support and/or immobilize the lower limb 11 to provide the affected lower limb 11 with substantial independent rehabilitative benefit.

The base assembly 26 is a unitary structure having an outer sole 30, a rib network 32, first and second sidewalls 34a, 34b and a heel plate retention segment 35. The outer sole 30 is a continuous piece extending along the bottom of the base assembly 26 and generally dimensioned in correspondence with the length and width of the foot. As such, the outer sole 30 extends essentially the entire length of the foot portion 16 of the internal boot 12 when the orthopedic walker boot 10 is worn on the lower limb 11. The bottom of the outer sole 30 preferably includes a layer of an elastomeric material which forms a walking surface 36 of the outer sole 30. The walking surface 36 has a tread pattern formed thereon to enhance the traction of the walking surface 36. The rib network 32 extends from the top of the outer sole 30 to enhance the structural rigidity of the outer sole 30. The rib network 32 prevents substantial flexion of the outer sole 30 when functioning as a walking platform.

Figure 5:
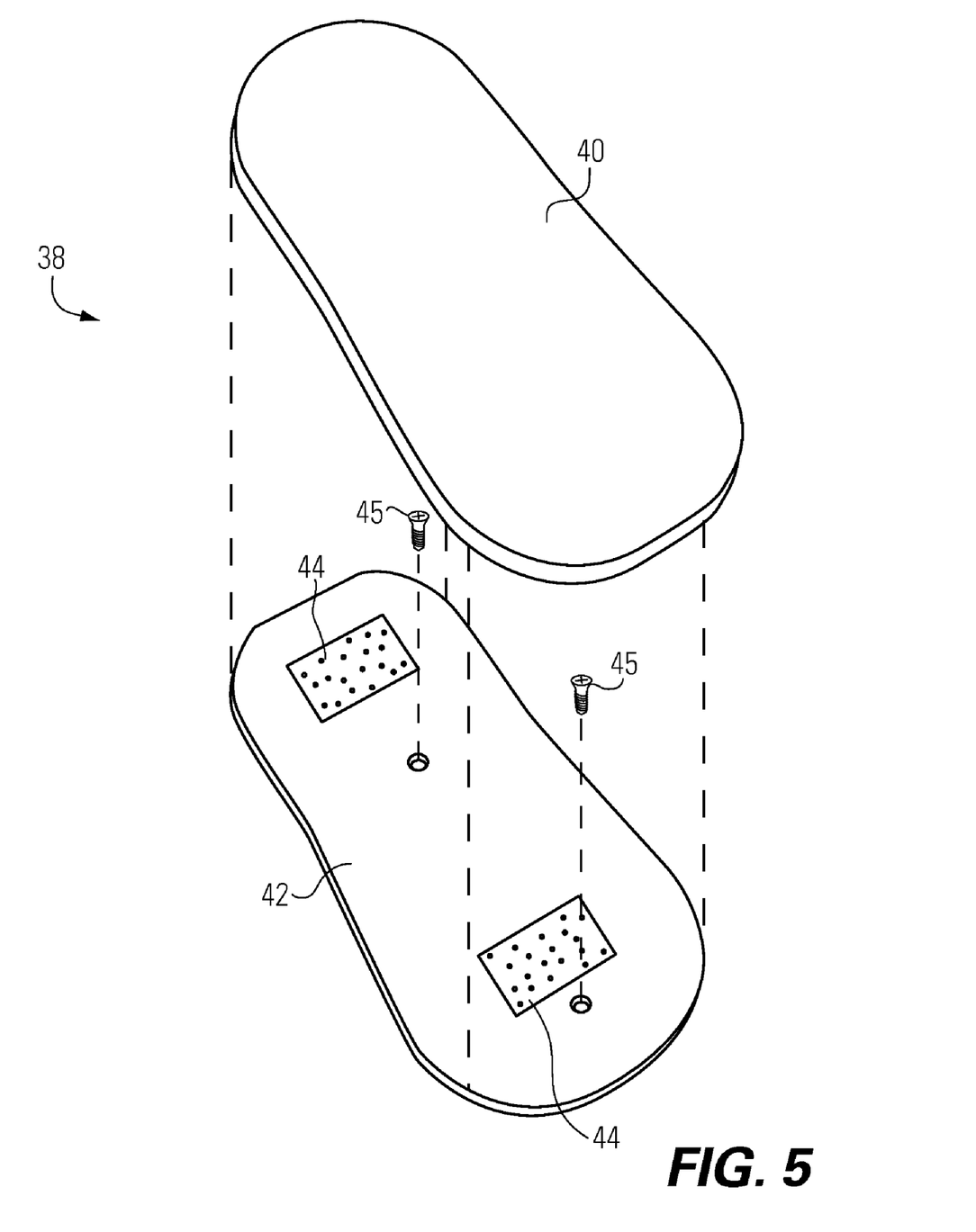
FIG. 5 is an exploded front perspective view of an insole included in the orthopedic walker boot of FIG. 1.

Referring additionally to FIG. 5, an insole 38 is preferably positioned atop the rib network 32 opposite the outer sole 30 to supplement the cushioning of the internal boot 12 along the sole of the foot of the wearer when the orthopedic walker boot 10 is worn on the lower limb 11. The insole 38 is generally dimensioned in correspondence with the outer sole 30. The insole 38 has two layers a cushion layer 40 positioned atop a stiffened layer 42. The cushion layer 40 is preferably formed from a cloth-foam-cloth laminate and the stiffened layer 42 is preferably formed from a flexible plastic which is substantially stiffer than the cushion layer 40. Releasable VELCRO fasteners are provided to retain the stiffened layer 42 in engagement with the cushion layer 40. The cloth forming the exterior of the cushion layer 40 constitutes the loop material of the VELCRO fasteners and patches 44 affixed to the stiffened layer 42 at appropriate locations thereon constitute the hook material of the VELCRO fasteners. Threaded screw fasteners 45 are also provided which extend through the stiffened layer 42 and fasten the stiffened layer 42 to the rib network 32 by means of correspondingly threaded screw holes 46 formed in the rib network 32.

With continuing reference to FIG. 4, the first and second sidewalls 34a, 34b are positioned at the opposing medial and lateral sides of the outer sole 30, respectively, adjacent to the ankle when the orthopedic walker boot 10 is worn on the lower limb 11. The heel plate retention segment 35 is posteriorly positioned on the base assembly 26 and extends above and along the posterior perimeter of the outer sole 30 between the first and second sidewalls 34a, 34b. The heel plate retention segment 35 is essentially perpendicular to the outer sole 30.

The first and second sidewalls 34a, 34b extend relatively higher than the heel plate retention segment 35 above and along the perimeter of the outer sole 30 from the medial and lateral sides thereof. The first and second sidewalls 34a, 34b are likewise essentially perpendicular to the outer sole 30. The first sidewall 34a has a first mount 47a formed thereon, to which the first upright 28a is fixably attached by fixable fasteners 48, such as rivets. The second sidewall 34b similarly has a second mount 47b formed thereon, to which the second upright 28b is fixably attached by fixable fasteners 48. As such, the first and second mounts 47a, 47b provide substantially immobile joints between the first upright and sidewall 28a, 34a and the second upright and sidewall 28b, 34b, respectively.

The first and second uprights 28a, 28b extend upward from the first and second mounts 38a, 38b, respectively, essentially the entire length of the leg portion 18 of the internal boot 12 when the internal boot 12 is positioned within the external shell 14. Releasable VELCRO fasteners are provided to retain the leg portion 18 of the internal boot 12 in engagement with the first and second uprights 28a, 28b of the external shell 14. The cloth forming the exterior of the internal boot 12 constitutes the loop material of the VELCRO fasteners and patches 50 affixed to the inside faces of the first and second uprights 28a, 28b at appropriate locations thereon constitute the hook material of the VELCRO fasteners.

The external shell 14 further comprises a plurality of paired strap guides 52 and a plurality of paired strap slots 53. The strap guides 52 are affixed to the first and second uprights 28a, 28b with one strap guide 52 of each pair affixed to the first upright 28a and the other strap guide 52 of the same pair affixed to the opposing second upright 28b. The strap slots 53 are formed in the first and second sidewalls 34a, 34b with one strap slot 53 of each pair formed in the first sidewall 34a and the other strap slot 53 of the same pair formed in the opposing second sidewall 34b.

With continuing reference to FIGS. 1 and 2, the external shell 14 is also provided with a plurality of retention straps 54 which are among the non-rigid elements of the substantially rigid external shell 14. Each retention strap 54 has two ends. A strap loop 56 is fixably attached to one end of the retention strap 54 while the opposite end of the retention strap 54 is free. The free end of each retention strap 54 is threaded either through a pair of the strap guides 52 or a pair of the strap slots 53 such that each pair of the strap guides 52 and the strap slots 53 retains a retention strap 54 therein. The retention strap 54 is constructed from a loop material and a tab 58 of hook material is fixably attached to the free end of each retention strap 54. As such, each retention strap 54 and hook tab 58 in combination cooperatively defines a VELCRO fastener.

In order for the external shell 14 to receive the internal boot 12 therein, it is necessary to open the anterior of the external shell 14. The anterior is opened by maintaining the retention straps 54 threaded through their respective pair of strap guides 52 or strap slots 53, but in a fully slackened condition. Once the internal boot 12 is placed in the external shell 14 through its open anterior, the anterior of the external shell 14 is closed by tightening and fastening the retention straps 54 which is effected by pulling the free tab end of each retention strap 54 across the anterior of the external shell 14 and threading the tab end through the strap loop 56 attached to the opposite end of the retention strap 54. The tab end of the retention strap 54 is then doubled back over the length of the retention strap 54 which extends across the anterior of the external shell 14 and tensioned until a desired degree of tightness is attained. The hook tab 58 of the retention strap 54 is releasably attached to a desired point on the underlying surface of the length of the retention strap 54 extending across the anterior of the external shell 14. In this manner, the retention straps 54 securely retain the internal boot 12 within the external shell 14, thereby enabling the external shell 14 to function as a rigid support frame for the pliant internal boot 12.

Figure 6:
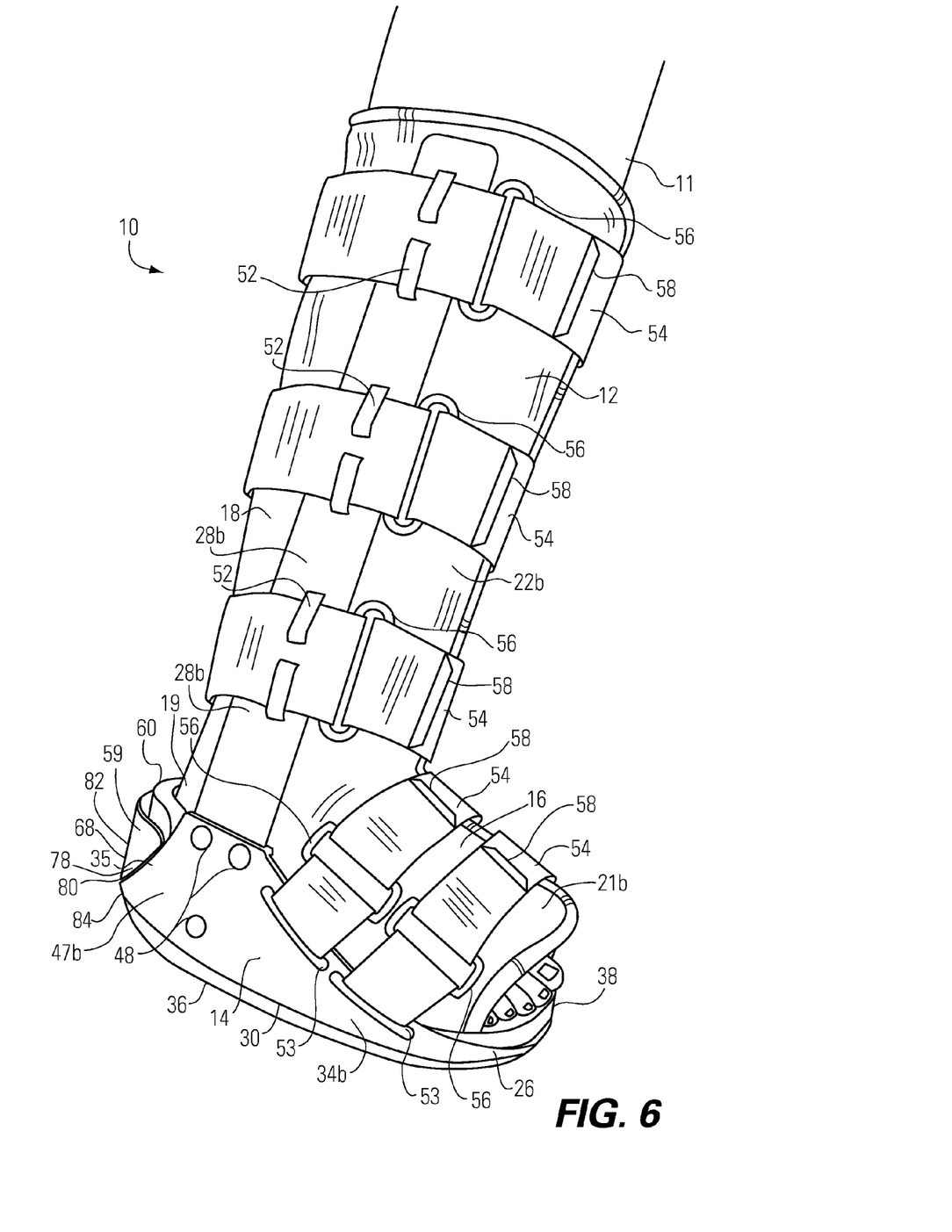
FIG. 6 is a side perspective view of the orthopedic walker boot of FIG. 1, but wherein the orthopedic walker boot has a closed-heel configuration.

In accordance with the present embodiment, the orthopedic walker boot 10, and specifically the external shell 14, have two selectively interchangeable configurations. FIGS. 1 and 4 both show the orthopedic walker boot 10, and specifically the external shell 14, in an open-heel configuration. FIG. 6 shows the same orthopedic walker boot 10 as FIG. 1, but in a closed-heel configuration. The closed-heel configuration of the orthopedic walker boot 10 is characterized by the attachment of a separate heel plate 59, which is selectively attachable or detachable, to the structure of the external shell 14. Accordingly, when the orthopedic walker boot 10 is in the closed-heel configuration, the heel plate 59 is in an attached condition, i.e., the heel plate 59 is posteriorly mounted on the external shell 14 as an optional supplemental structure. In contrast, when the orthopedic walker boot 10 is in the open-heel configuration shown in FIGS. 1 and 4, the heel plate 59 is in a detached condition, i.e., the heel plate 59 is omitted altogether from the structure of the external shell 14.

With reference to FIGS. 6-10, the heel plate 59 is preferably formed as a unitary structure from the same hard rigid material as the remainder of the external shell 14. A heel pad 60 configured in correspondence with the inside face of the heel plate 59 is releasably attached to the inside face 61 of the heel plate 59 by means of a releasable VELCRO fastener which comprises a patch of loop material (not shown) affixed to the heel pad 60 and a patch of hook material 62 affixed to the inside face 61 of the heel plate 59 or vice versa. The heel pad 60 is preferably formed from a pliant foam material which supplements the cushioning of the internal boot 12 at the heel of the wearer when the orthopedic walker boot 10 is worn on the lower limb 11. It is noted that the heel pad 60 is omitted from FIG. 10 for clarity.

Posteriorly mounting the heel plate 59 on the external shell 14 is enabled by two tracks 63a and 63b formed on the inside face 64 of the heel plate retention segment 35 at each medial and lateral end thereof and two corresponding cooperative guide runners 66a and 66b formed on a recessed lower portion 67 of the outside face 68 of the heel plate 59 at each medial and lateral end thereof. Each track 63a, 63b of the heel plate retention segment 35 comprises a pair of rails 70 preferably integrally formed with and protruding from the inside face 64 of the heel plate retention segment 35. The two rails 70 of each track 63a, 63b are spaced slightly apart from one another as the rails 70 extend longitudinally vertically in parallel relation to one another along the inside face 64 of the heel plate retention segment 35.

Figure 10:
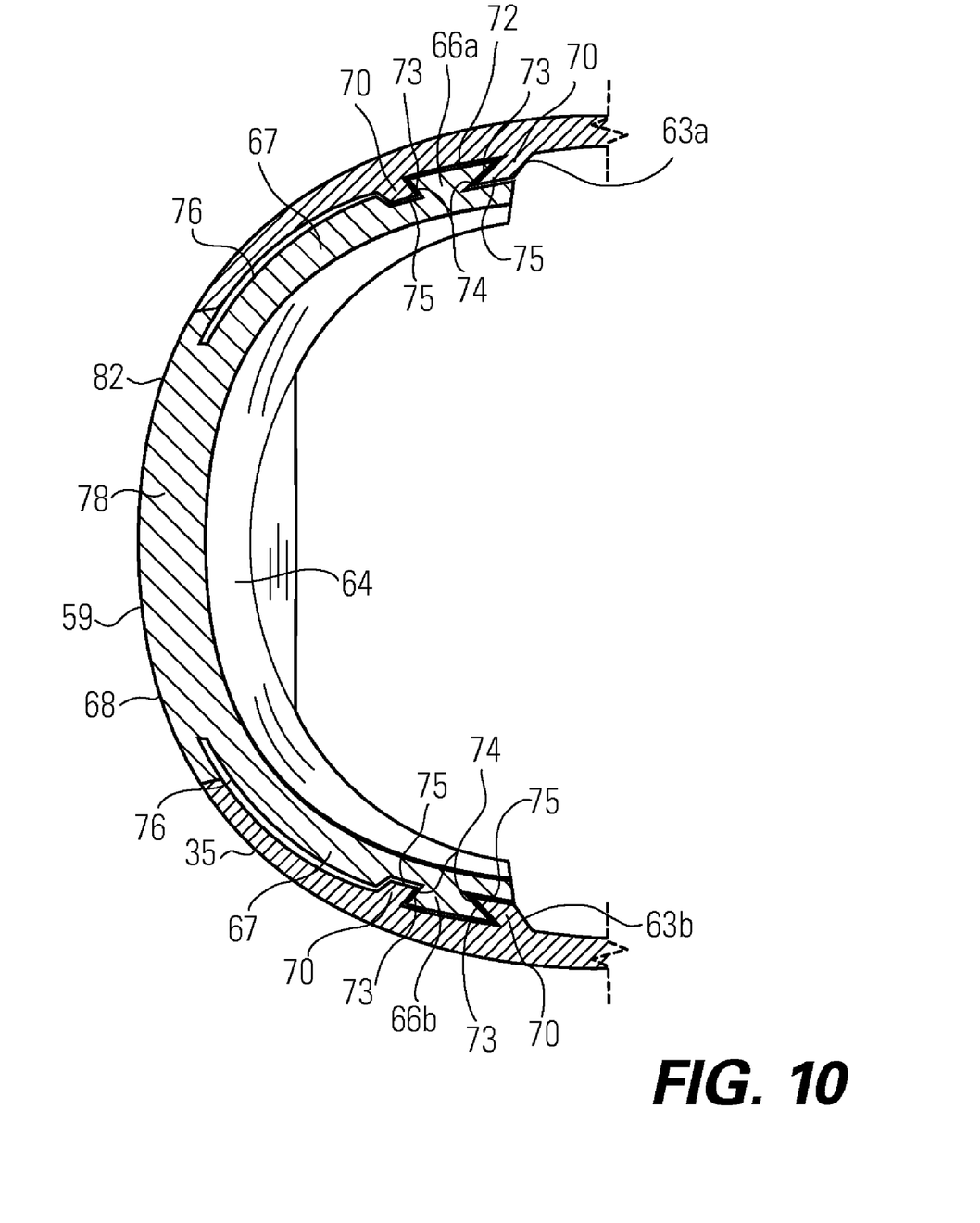
FIG. 10 is a downward-facing cross-sectional view of the assembled heel plate and heel plate retention segment of the external shell included in the orthopedic walker boot of FIG. 6 which is taken partway down the heel plate.

The space between the two rails 70 defines a female retention slot 72 which is vertically bounded on either side by the respective longitudinal inside face 73 of each rail 70. The inside faces 73 of the rails 70 are beveled in relation to the inside face 64 of the heel plate retention segment 35 such that the horizontal cross-section of the retention slot 72 has an essentially trapezoidal configuration.

Figure 7:
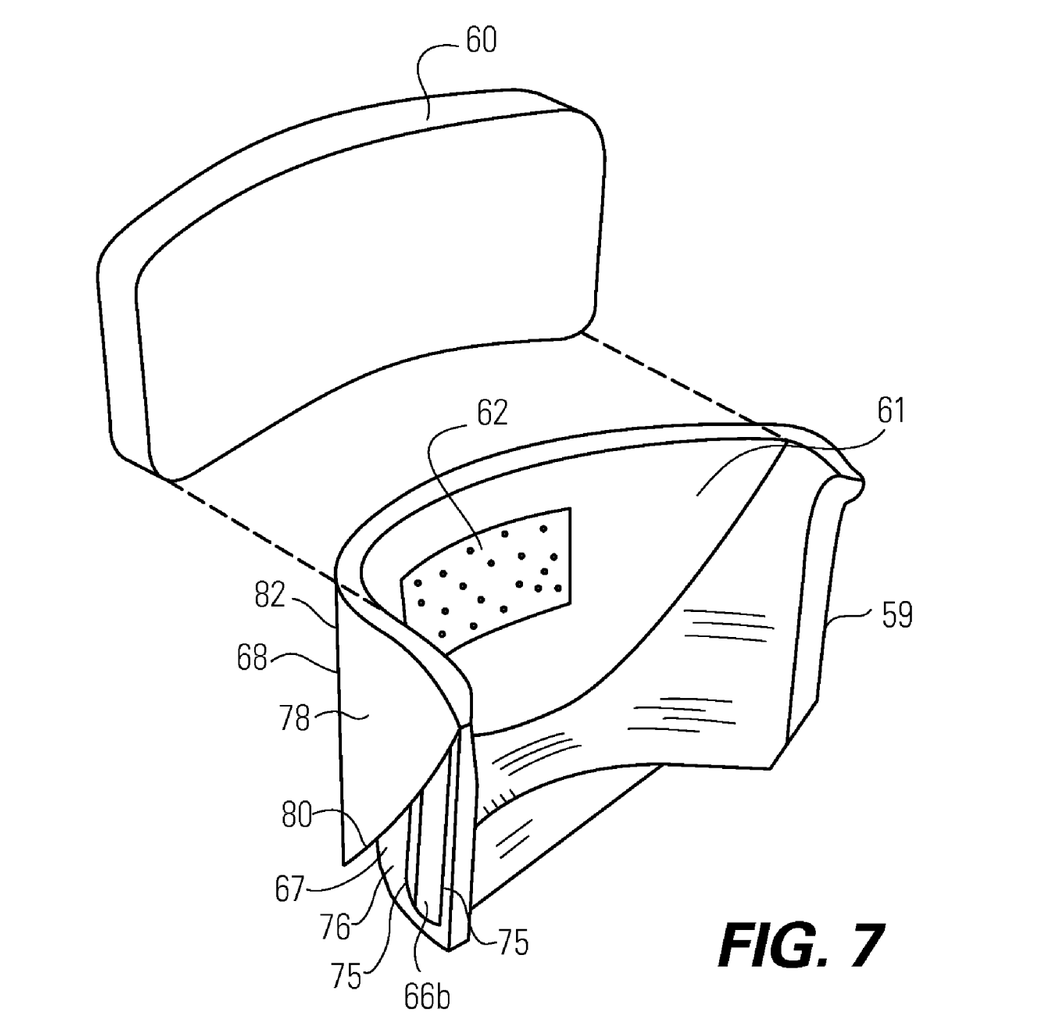
FIG. 7 is a front perspective view of a heel plate included in the orthopedic walker boot of FIG. 6.
Figure 8:
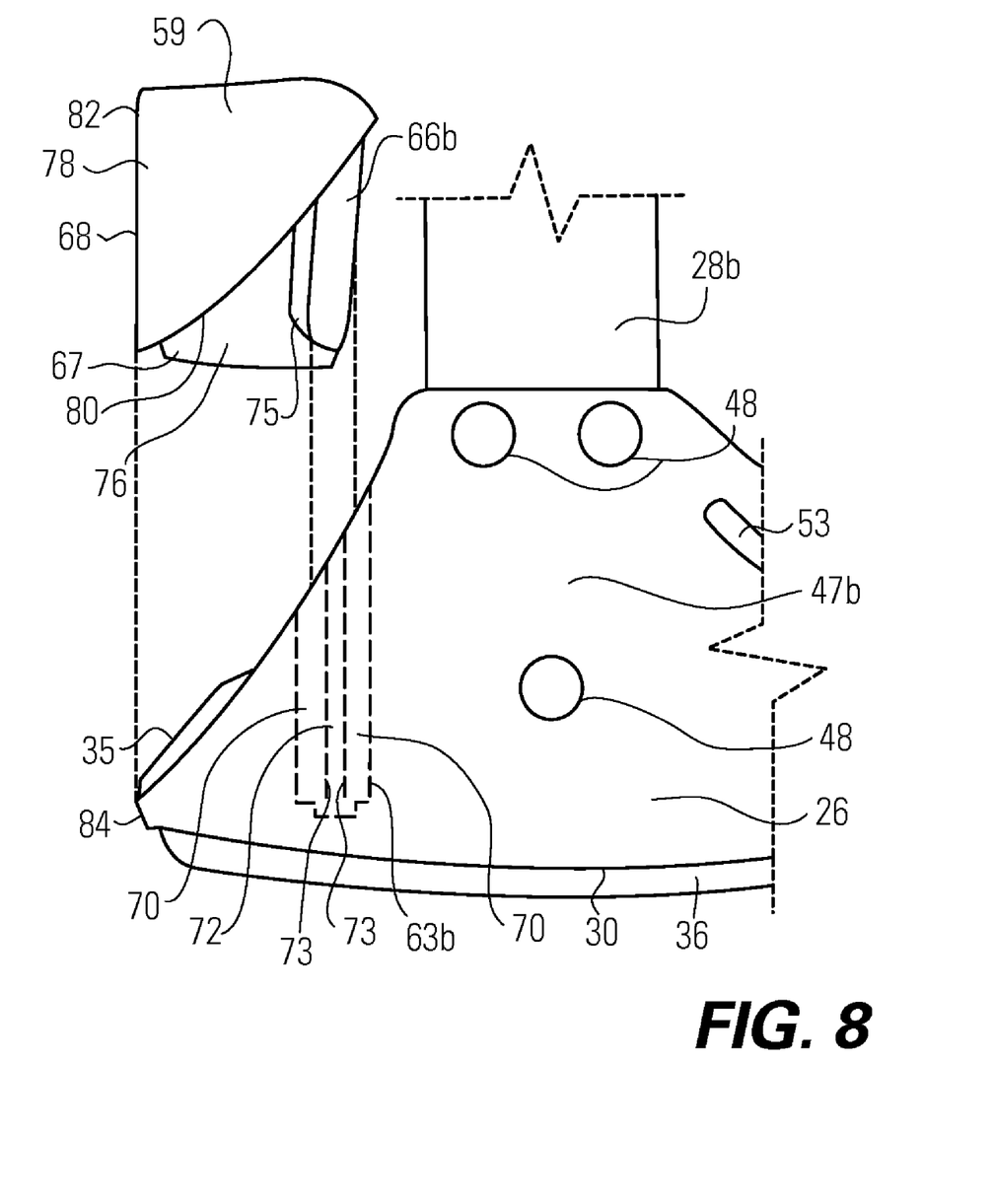
FIG. 8 is an exploded side elevational view of the heel plate and a heel plate retention segment of the external shell included in the orthopedic walker boot of FIG. 6.

Each guide runner 66a, 66b of the heel plate 59 comprises a single runner preferably integrally formed with and protruding from the recessed lower portion 67 of the outside face 68 of the heel plate 59 and extends longitudinally and vertically along the lower portion 67 of the outside face 68. The inside faces 74 of each guide runner 66a, 66b are beveled in relation to the inside face 64 of the heel plate retention segment 35, but in the opposite direction as the beveled inside faces 73 of the rails 70. Accordingly, the retention slots 72 and guide runners 66a, 66b are correspondingly sized and configured relative to one another such that each female retention slot 72 is able to slidably receive and retain the respective male guide runner 66a, 66b therein when the practitioner desires to effect releasable attachment of the heel plate 59 to the heel plate retention segment 35.

A pair of clearance indentations 75 are also provided in the recessed lower portion 67 of the outside face 68 of the heel plate 59 adjacent to the guide runner 66a, 66b. The clearance indentations 75 are sized and configured in correspondence with the rails 70 such that the clearance indentations 75 are able to slidably receive an adjacent rail 70 when the guide runner 66a, 66b is received in the retention slot 72, thereby facilitating close fitting engagement of the heel plate 59 with the heel plate retention segment 35. The recessed configuration of the lower portion 67 of the outside face 68 of the heel plate 59 also enables the outside surface 76 of the lower portion 67 to slide into close fitting engagement with the inside face 64 of the heel plate retention segment 35 when the guide runner 66a, 66b is received in the retention slot 72, thereby further facilitating close fitting engagement of the heel plate 59 with the heel plate retention segment 35.

When the heel plate 59 is in the attached condition posteriorly mounted on the external shell 14, the outside face 68 of the heel plate 59 has a protruding upper portion 78 which extends upwardly away from the heel plate retention segment 35 essentially perpendicular to the outer sole 30. The protruding upper portion 78 of the outside face 68 has a bottom edge 80 which is aligned and continuously engaged with the posterior top edge of the heel plate retention segment 35. The upper portion 78 of the outside face 68 of the heel plate 59 also has an outside surface 82 which extends above and is continuous with the outside face 84 of the heel plate retention segment 35. Accordingly, the outside surface 82 of the upper portion 78 and the outside face 84 of the heel plate retention segment 35 form a smooth continuous surface on the posterior of the orthopedic walker boot 10.

The heel plate 59 in the attached condition covers, either entirely or at least partially, the heel portion 19 of the internal boot 12 and the heel of the lower limb 11 disposed therein. As such, the heel plate 59 provides a strong impact-resistant rigid protective cover for the posterior face of the wearer's heel, which substantially supplements the limited protection afforded by the heel portion 19 of the pliant internal boot 12. It is particularly advantageous to use the closed-heel configuration of the orthopedic walker boot 10 where the wearer commonly participates in everyday activities which could otherwise lead to potentially painful impacts against the heel from objects in the external surroundings.

Figure 11:
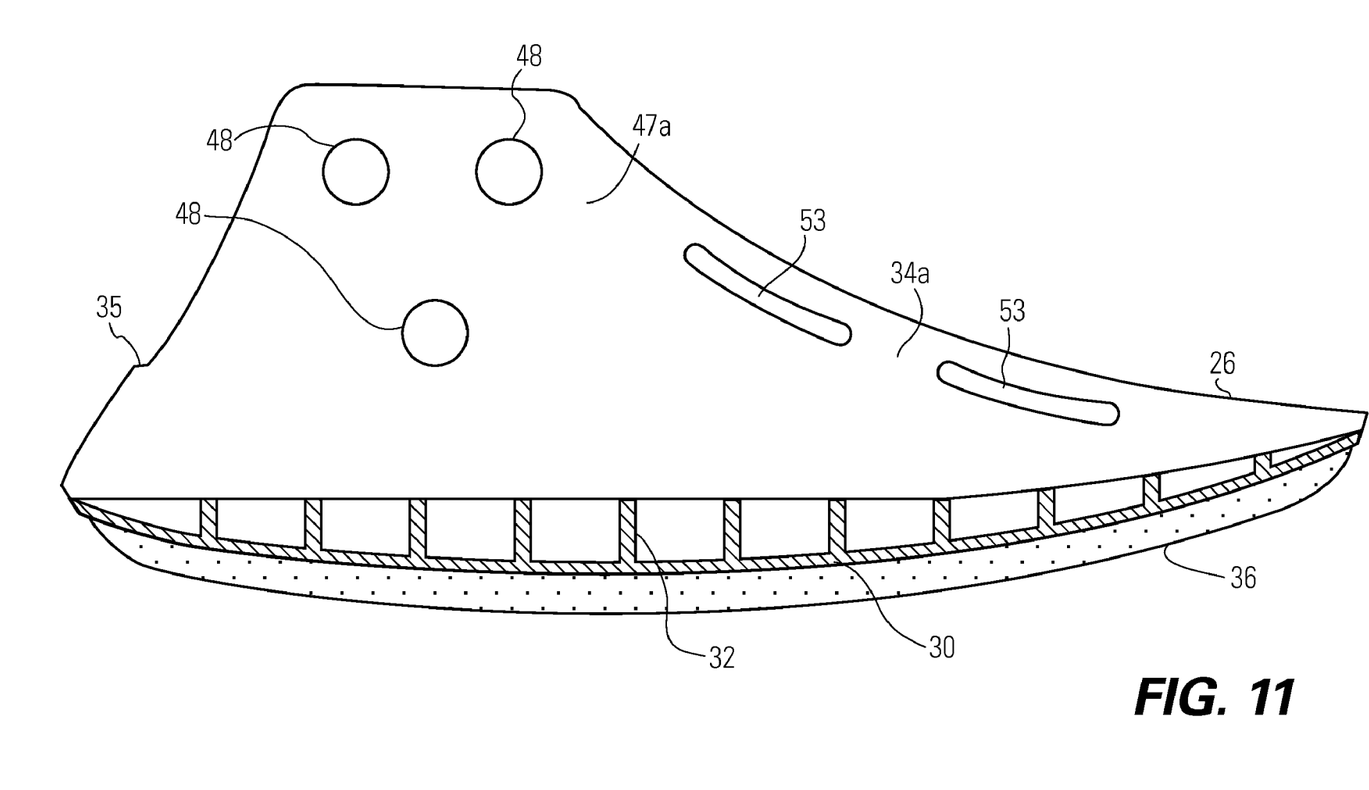
FIG. 11 is a cross-sectional view of the outer sole of the external shell included in the orthopedic walker boot of FIG. 1 which is taken along the longitudinal axis of the outer sole.
Figure 12:
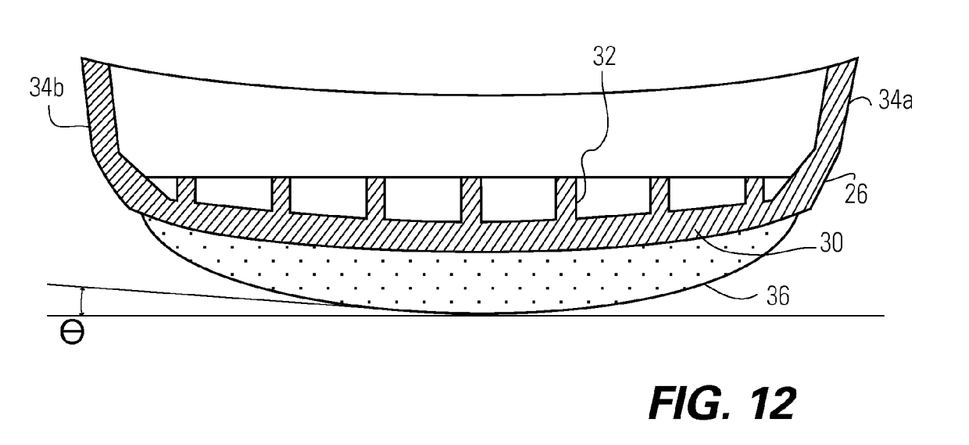
FIG. 12 is a cross-sectional view of the outer sole of the external shell included in the orthopedic walker boot of FIG. 1 which is taken along the latitudinal axis of the outer sole.

The orthopedic walker boot 10 of the present embodiment, and specifically the external shell 14, is further characterized as having two essentially perpendicular curved axes on the walking surface 36 of its outer sole 30 in the manner described below. Referring to FIGS. 11 and 12, the arcuate configuration of the walking surface 36 of the outer sole 30 is shown along two different axes. In particular, the walking surface 36 is curved along essentially the entire the length of its central longitudinal axis as shown in FIG. 11. The walking surface 36 is also curved along essentially the entire width of its central latitudinal axis, which is essentially perpendicular to the longitudinal axis, as shown in FIG. 12.

The degree of longitudinal curvature of the walking surface 36 is preferably essentially continuous and constant along its entire length. It is further noted that although the cross-sectional view of FIG. 11 is taken along the central longitudinal axis of the walking surface 36, this cross-sectional view would preferably appear essentially the same with respect to longitudinal curvature if taken along any other longitudinal line through the walking surface 36 away from, but parallel to, the central longitudinal axis. Similarly, the degree of latitudinal curvature of the walking surface 36 is preferably essentially continuous and constant along its entire width. Although the cross-sectional view of FIG. 12 is taken along the central latitudinal axis of the walking surface 36, this cross-sectional view would also preferably appear essentially the same with respect to latitudinal curvature if taken along any other latitudinal line through the walking surface 36 away from, but parallel to, the central latitudinal axis.

Constructing the outer sole 30 of the external shell 14 with two curved axes on its walking surface 36 beneficially facilitates both the longitudinal and latitudinal rolling of the foot in the normal walking gait when one is engaged in walking activity while wearing the orthopedic walker boot 10 on a lower limb 11. In some cases, only a slight degree of curvature in the axes achieves the desired benefit. For example, in accordance the embodiment shown in FIG. 12, a beneficial effect is achieved when the curvature of the latitudinal axis is characterized by only a slight angle $\theta$ of 2° as one moves latitudinally away from the longitudinal center line of the walking surface 36.

While the forgoing preferred embodiments of the invention have been described and shown, it is understood that alternatives and modifications, such as those suggested and others, may be made thereto and fall within the scope of the invention.

We claim:

1. An orthopedic walker boot comprising:
    a substantially rigid external shell configured to receive a lower limb of a wearer, wherein said external shell includes an inner platform having an outer perimeter sized in substantial correspondence with the outer perimeter of the sole of the foot on the lower limb such that said outer perimeter of said inner platform substantially encircles the outer perimeter of the sole of the foot when the lower limb is received in said external shell and further wherein said inner platform is substantially horizontally aligned when the wearer is standing with the lower limb received in said external shell; and
    a substantially rigid heel plate selectively transitionable between a detached condition and an attached condition with respect to said external shell, wherein said external shell has an open-heel configuration when said heel plate is in said detached condition and said external shell has a closed-heel configuration when said heel plate is in said attached condition and further wherein said heel plate in said attached condition is substantially vertically aligned perpendicular to said inner platform when the wearer is standing with the lower limb received in said external shell and said heel plate extends posteriorly around said external shell in substantially continuous correspondence with a posterior edge of said outer perimeter of said internal platform such that said heel plate forms a substantially continuous shield around the vertical posterior face of the heel of the foot.

2. The orthopedic walker boot of claim 1, wherein said external shell has a heel plate retention segment including a retention slot.

3. The orthopedic walker boot of claim 2, wherein said heel plate has an outside face with a protruding upper portion having a bottom edge and an outside surface, said heel plate has a recessed lower portion having an outside surface, and said heel plate retention segment has an inside face, an outside face, and a top edge, further wherein said outside surface of said lower portion slidably engages said inside face of said heel plate retention segment and said bottom edge of said upper portion engages said top edge of said heel plate retention segment when said heel plate is in said attached condition.

4. The orthopedic walker boot of claim 3, wherein said bottom edge of said upper portion continuously engages said top edge of said heel plate retention segment when said heel plate is in said attached condition such that said outside surface of said upper portion in combination with said outside face of said heel plate retention segment forms an essentially smooth continuous posterior surface of said orthopedic walker boot.

5. The orthopedic walker boot of claim 1, wherein said heel plate has a guide runner.

6. The orthopedic walker boot of claim 1, wherein said external shell has a heel plate retention segment including a retention slot and said heel plate has a guide runner, further wherein said retention slot is configured to slidably receive said guide runner therein when said heel plate is in said attached condition and to slidably discharge said guide runner when said heel plate is in said detached condition.

7. The orthopedic walker boot of claim 1 further comprising an internal boot positioned in said external shell, wherein said internal boot is sized to substantially enclose the ankle and foot of the lower limb of the wearer when the lower limb is received in said external shell.

8. An orthopedic walker boot comprising:
    a rigid external shell configured to receive a lower limb of a wearer;
    a selectively removable substantially rigid heel plate having a detached condition and an attached condition to provide said external shell with an open-heel configuration or a closed-heel configuration, respectively; and
    a pliant internal boot positioned in said external shell, wherein said internal boot is sized to substantially enclose the ankle and foot of the lower limb of the wearer, further wherein said heel plate in said attached condition is continuously positioned adjacent to the vertical posterior surface of the heel when the lower limb is received in said external shell and substantially continuously shields the vertical posterior surface of the heel of the foot, and further wherein said heel plate in said detached condition does not substantially shield the vertical posterior surface of the heel.

9. The orthopedic walker boot of claim 8, wherein said external shell has a heel plate retention segment including a retention slot and said heel plate has a guide runner, further wherein said retention slot is configured to slidably receive said guide runner therein when said heel plate is in said attached condition and to slidably discharge said guide runner when said heel plate is in said detached condition.

10. The orthopedic walker boot of claim 9, wherein said heel plate has an outside face with a protruding upper portion having a bottom edge and an outside surface, said heel plate has a recessed lower portion having an outside surface, and said heel plate retention segment has an inside face, an outside face, and a top edge, further wherein said outside surface of said lower portion slidably engages said inside face of said heel plate retention segment and said bottom edge of said upper portion engages said top edge of said heel plate retention segment when said heel plate is in said attached condition.

11. The orthopedic walker boot of claim 10, wherein said bottom edge of said upper portion continuously engages said top edge of said heel plate retention segment when said heel plate is in said attached condition such that said outside surface of said upper portion in combination with said outside face of said heel plate retention segment forms an essentially smooth continuous posterior surface of said orthopedic walker boot.

* * * * *